United States Patent [19]

Credner et al.

[11] 4,060,617
[45] Nov. 29, 1977

[54] ESTERS OF THE OPHYLLINYLACETIC ACID

[75] Inventors: Karl Credner, Kaarst; Berthold Geisel, Gronau, Leine; Gunter Brenner, Grefrath; Manfred Tauscher, Gronau, Leine, all of Germany

[73] Assignee: Johann A. Wulfing, Germany

[21] Appl. No.: 672,838

[22] Filed: Apr. 1, 1976

[51] Int. Cl.$^2$ .................... A61K 31/52; C07D 473/08
[52] U.S. Cl. .................... 424/253; 260/254; 260/256
[58] Field of Search .............. 260/256, 254; 424/253

[56] References Cited

U.S. PATENT DOCUMENTS

| | | | |
|---|---|---|---|
| 2,756,229 | 7/1956 | Stoll | 260/256 |
| 2,878,251 | 3/1959 | Zirm et al. | 260/256 |
| 3,935,196 | 1/1976 | Higuchi et al. | 260/256 |
| 3,984,413 | 10/1976 | Metz et al. | 200/256 |

Primary Examiner—Paul M. Coughlan, Jr.
Attorney, Agent, or Firm—Jacobs & Jacobs

[57] ABSTRACT

A compound of the formula

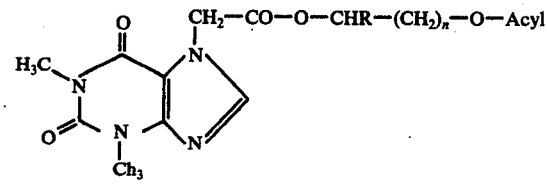

wherein R is hydrogen or methyl, n is a number from 1 to 4 and 'Acyl' is nicotinoyl, 3-methylpyrazole-5-carboyl, 3-methyl-isoxazolyl-5-carboyl, 5-n-butylpyridin-2-carboyl, 2-(4-chlorophenoxy)-2-methyl-propionyl, 2-acetoxybenzoyl or theophyllinyl-7-acetyl, are useful for their effect on serum lipoids and, in particular, for treating adverse hyperlipidemic states in humans.

48 Claims, No Drawings

ESTERS OF THE OPHYLLINYLACETIC ACID

The present invention relates to pharmaceutically active compounds, to their preparation and to compositions containing them.

A common problem encountered when administering medicaments is that they sometimes tend to become less effective than expected in bringing about the desired pharmacological effect because of the so called 'Rebound Effect'. It has been discovered that this problem can be reduced for certain acidic medicaments if they are administered in the form of certain esters. Furthermore use of certain of these esters can also prolong the effective period after administration.

Accordingly the present invention provides compounds of the formula (I):

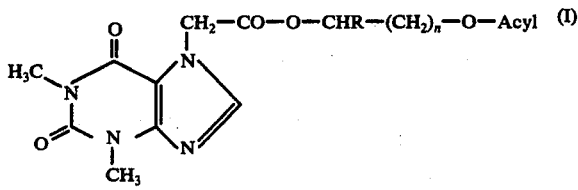

wherein R is a hydrogen atom or a methyl group; n is a number from 1 to 4 and 'Acyl' is a nicotinoyl, 3-methylpyrazole-5-carboyl, 3-methylisoxazolyl-5-carboyl, 5-n-butylpyridin-2-carboyl, 2-(4-chlorophenoxy)-2-methyl-propionyl, 2-acetoxybenzoyl or theophyllinyl-7-acetyl group.

Suitably 'Acyl' is a nicotinoyl, 3-methylpyrazole-5-carboyl, 5-n-butylpyridin-2-carboyl, 2-(4-chlorophenoxy)-2-methyl-propionyl, 2-acetoxybenzoyl or theophyllinyl-7-acetyl group.

Particularly suitable compounds of the formula (I) which have improved pharmacodynamic properties include those of the formula (II):

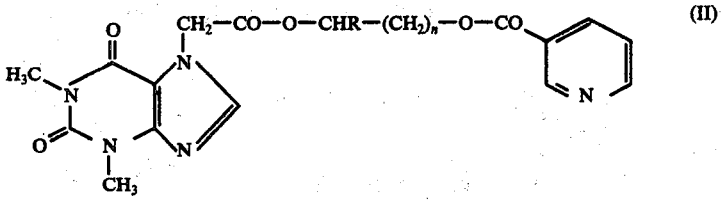

wherein n and R are as defined in relation to formula (I).

Most suitable R in the compounds of the formulae (I) and (II) represents a hydrogen atom.

Most suitably n in the compounds of the formulae (I) and (II) is 1 or 2.

A particularly favoured -CHR-(CH$_2$)$_n$- residue in the compounds of formulae (I) and (II) is the -CH$_2$-CH$_2$- group.

A preferred compound of this invention is 1-(theophyllinyl-7-methylenecarboyloxy)-2-(nicotinoyloxy)ethane which has particularly acceptable pharmacological effects on serum lipids.

The present invention also provides a process for the preparation of the compounds of the formula (I) which process comprises:

a. The reaction of a compound of the formula (III):

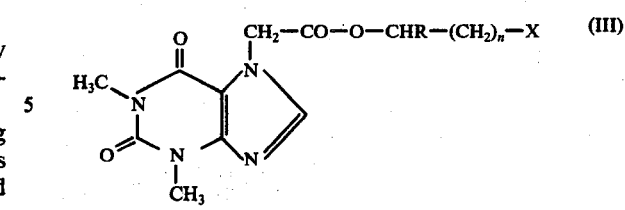

with a compound of the formula (IV):

HO·Acyl                                                IV or an acylating derivative thereof, wherein R, n and Acyl are as defined in relation to formula (I) and X is a hydroxyl group or a readily displaceable group; or b. The reaction of a compound of the formula (V):

X - CHR - (CH$_2$)$_n$ - O - Acyl               V with theophyllinylacetic acid or an acylating derivative thereof; wherein R, n and Acyl are as defined in relation to formula (I) and X is a hydroxyl group or a readily displaceable group.

For the reaction of a compound of the formula (III) or (V) wherein X is a hydroxyl group suitable compounds of the formula (IV) or suitable derivatives of theophyllinylacetic acid include the free acid in the presence of a dehydrating agent such as dicyclohexyl-carbodiimide, or derivatives of the free acid such as an acid halide such as the acid chloride or the acid anhydride or mixed anhydride.

For the reaction of a compound of the formulae (III) or (V) wherein X is a displaceable group such as a chlorine, bromine or iodine atom or an activated ester such as a methane sulphonyl or toluene sulphonyl ester, the preferred derivative of the compound of formula (IV) or of theophyllinylacetic acid is a salt such as an alkali metal or like salt, for example the sodium salt.

The preceding reactions can be brought about under conditions conventionally used for the preparation of esters.

Suitable solvents for such reactions include inert organic solvents such as dimethylformamide, benzene, pyridine or the like.

The present invention also provides a pharmaceutical composition which comprises a compound of the formula (I) together with a pharmaceutically acceptable carrier.

The compositions of the invention are specially useful in treating adverse hyperlipiedemic states in humans. For such treatment, the compounds are generally administered orally although parenteral methods of administration may also be used.

Typical oral formulations will include tablets, pills, capsules, sachets, granules, powders, chewing gum, suspensions, emulsions and solutions, particularly preferred oral formulations are tablets and capsules. Where appropriate, the formulations may include conventional diluents, binding agents, dispersing agents, surface-active agents, lubricating agents, coating materials, flavouring agents, colouring agents, solvents, thickening agents, suspending agents, sweeteners or any other pharmaceutically acceptable additives, for example, gelatin, lactose, starch, talc, magnesium stearate, hydrogenated oils, polyglycols and syrups. Where the formulations are tablets or capsules and the like, they will represent pre-measured unit doses but in the case of granules, powders, suspensions and the like, the formulations may be presented as pre-measured unit doses or in multi-dose containers from which the appropriate unit dose may be withdrawn.

Injectable compositions may be as aqueous or non-aqueous solutions, suspensions or emulsions in a pharmaceutically acceptable liquid.

Preferred dosage forms of the composition will be conventional tablets or capsules containing a pre-measured dose for oral administration. Such dosage forms will normally contain between 10 and 500 mgs of compound of formula (I) and preferably between 25 and 300 mgs. Such dosage forms will normally be taken from 1 to 6 times daily. The maximum daily dose for a 70 kg adult will not normally exceed 1,500 mgs and a daily dose of not more than 1,000 mgs is generally preferred. Normally, the daily dose for a 70 kg adult will be at least 25 mgs and usually at least 50 mgs.

The compositions of the invention may be prepared by conventional methods of mixing, blending, tabletting and the like.

The following Examples illustrate the invention:

EXAMPLE 1

1-(Theophyllinyl-7-methylencarboyloxy)-2-(nicotinoyl)ethane

Theophyllinyl-7-acetic acid β-hydroxyethyl ester (56.5 g), pyridine (32 ml) and chloroform (500 ml) were stirred together for an hour. To this was added nicotinoylchloride hydrochloride (42 g) in a mixture of chloroform (200 ml) and pyridine (32 ml). The reaction was stirred for 24 hours at room temperature. The reaction mixture was diluted with water (500 ml) and the chloroform phase separated, dried and evaporated to yield a crystalline material (77.1 g). A sample of this material recrystallised from water yielded the desired compound (m.p. 187° C).

The title compound has an oral $LD_{50}$ in rats of greater than 1g/kg. When administered to 17 hour starved rats at 300 mg/kg the title compound produced a fall in serum triglyceride and cholesterol of about 30% each at 1 hour post dose.

An analogous procedure may be used to prepare 1-(theophyllinyl-7-methylenecarboyloxy)-4-(nicotinoyl)butane, m.p. 148° - 150° C.

EXAMPLE 2

2-(Theophyllinyl-7-methylencarboyloxy)-3-(nicotinoyloxy)propane

Nicotinic acid-2-hydroxypropyl ester (15.03 g) was dissolved in pyridine (100 ml). To this was added dropwise over 1 hour theophyllinyl-7-methylen-carboyl chloride (21.33 g) in chloroform (250 ml). The reaction mixture was maintained at room temperature for 24 hours and then the solvent removed by evaporation. The residue was taken up in chloroform (400 ml) and washed with sodium carbonate solution (3 × 100 ml) and dried (sodium sulphate). The chloroform was removed by evaporation to yield a brownish crystalline material (28.1 g). The product was recrystallised from ethyl acetate to yield the desired compound m.p. 137° C.

We claim:

1. A compound of the formula (I):

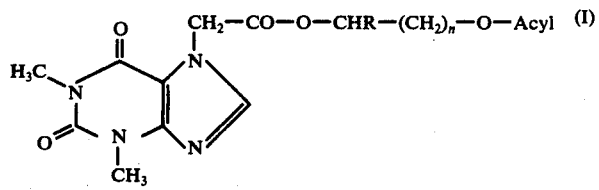

wherein R is hydrogen or methyl; n is a number from 1 to 4 and 'Acyl' is nicotinoyl, 3-methylpyrazole-5-carboyl, 3-methyl-isoxazolyl-5-carboyl, 5-n-butylpyridin-2-carboyl, 2-(4-chlorophenoxy)-2-methyl-propionyl, 2-acetoxybenzoyl or theophyllinyl-7-acetyl.

2. A compound according to claim 1 wherein 'Acyl' is nicotinoyl, 3-methylpyrazole-5-carboyl, 5-n-butyl-pyridin-2-carboyl, 2-(4-chlorophenoxy)-2-methylpropionyl, 2-acetoxybenzoyl or theophyllinyl-7-acetyl.

3. A compound according to claim 2 wherein 'Acyl' is nicotinoyl.

4. A compound of the formula (II):

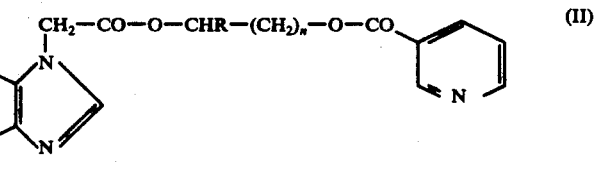

wherein R is hydrogen or methyl and n is a number from 1 to 4.

5. A compound according to claim 1 wherein n is 1.

6. A compound according to claim 1 wherein R is hydrogen.

7. A compound according to claim 1 wherein the -CHR-$(CH_2)_n$- residue is a -$CH_2$-$CH_2$- group.

8. The compound according to claim 1 which is 1-(theophyllinyl-7-methylenecarboyloxy)-2-(nicotinoyloxy)ethane.

9. A compound according to claim 4 wherein R is hydrogen.

10. A compound according to claim 4 wherein n is 1.

11. A compound according to claim 1 wherein n is 1 or 2.

12. A compound according to claim 4 wherein n is 1 or 2.

13. The compound according to claim 1 which is 1-(theophyllinyl-7-methylenecarboyloxy)-4-(nicotinoyloxy)butane.

14. The compound according to claim 1 which is 2-(theophyllinyl-7-methylenecarboyloxy)-3-(nicotinoyloxy)propane.

15. A pharmaceutical composition in oral or parenteral administration form useful for treating adverse hyperlipidemic states in humans which comprises a therapeutically effective amount of a compound of the formula (I):

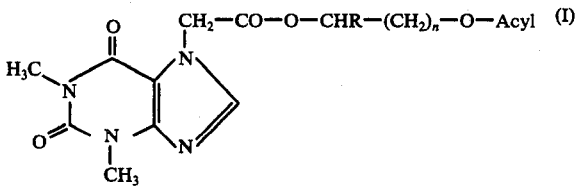

wherein R is hydrogen or methyl, n is a number from 1 to 4 and 'Acyl' is nicotinoyl, 3-methylpyrazole-5-carboyl, 3-methylisoxazolyl-5-carboyl, 5-n-butylpyridin-2-carboyl, 2-(4-chlorophenoxy)-2-methyl-propionyl, 2-acetoxybenzoyl or theophyllinyl-7-acetyl, in combination with a pharmaceutically acceptable carrier.

16. A composition according to claim 15 wherein 'Acyl' is nicotinoyl, 3-methylpyrazole-5-carboyl, 5-n-butylpyridin-2-carboyl, 2-(4-chlorophenoxy)-2-methyl-propionyl, 2-acetoxybenzoyl or theophyllinyl-7-acetyl.

17. A composition according to claim 16 wherein 'Acyl' is nitcotinoyl.

18. A pharmaceutical composition in oral or parenteral administration form useful for treating adverse hyperlipidemic states in humans which comprises a therapeutically effective amount of a compound of the formula (II):

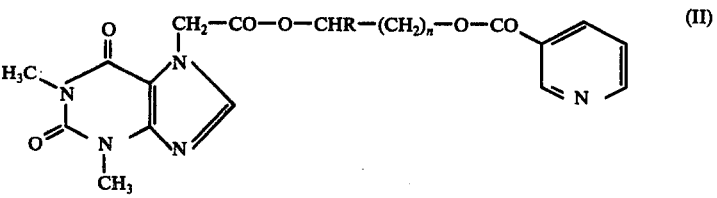

wherein R is hydrogen or methyl and n is a number from 1 to 4, in combination with a pharmaceutically acceptable carrier.

19. A composition according to claim 15 wherein n is 1.

20. A composition according to claim 15 wherein R is hydrogen.

21. A composition according to claim 15 wherein the -CHR-(CH₂)ₙ- residue is a -CH₂-CH₂- group.

22. A composition according to claim 15 wherein the compound is 1-(theophyllinyl-7-methylenecarboyloxy)-2-(nicotinoyloxy)ethane.

23. A composition according to claim 18 wherein R is hydrogen.

24. A composition according to claim 18 wherein n is 1.

25. A composition according to claim 15 wherein n is 1 or 2.

26. A composition according to claim 18 wherein n is 1 or 2.

27. A composition according to claim 15 wherein the compound is 1-(theophyllinyl-7-methylenecarboyloxy)-4-(nicotinoyloxy)butane.

28. A composition according to claim 15 wherein the compound is 2-(theophyllinyl-7-methylenecarboyloxy)-3-(nicotinoyloxy)propane.

29. A composition according to claim 15 in oral administration form.

30. A composition according to claim 15 in parenteral administration form.

31. A composition according to claim 15 in oral administration form wherein the compound is 1-(theophyllinyl-7-methylenecarboyloxy)-2-(nicotinoyloxy)ethane.

32. A method of treating adverse hyperlipidemic states in humans which comprises orally or parenterally administering a therapeutically effective amount of a compound of the formula (I):

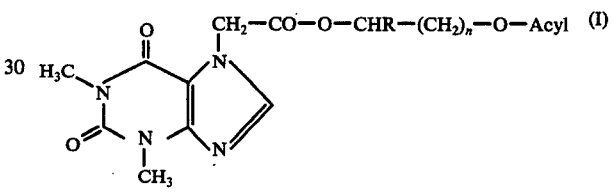

wherein R is hydrogen or methyl; n is a number from 1 to 4 and 'Acyl' is nicotinoyl, 3-methylpyrazole-5-carboyl, 3-methylisoxazolyl-5-carboyl, 5-n-butylpyridin-2-carboyl, 2-(4-chlorophenoxy)-2-methyl-propionyl, 2-acetoxybenzoyl or theophyllinyl-7-acetyl; in combination with a pharmaceutically acceptable carrier.

33. A method according to claim 32 wherein 'Acyl' is nicotinoyl, 3-methylpyrazole-5-carboyl, 5-n-butylpyridin-2-carboyl, 2-(4-chlorophenoxy)-2-methyl-propionyl, 2-acetoxybenzoyl or theophyllinyl-7-acetyl.

34. A method according to claim 32 wherein 'Acyl' is nicotinoyl.

35. A method of treating adverse hyperlipidemic states in humans which comprises orally or parenterally administering a therapeutically effective amount of a compound of the formula (II):

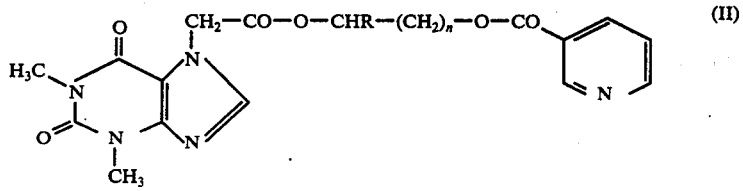

wherein R is hydrogen or methyl and *n* is a number from 1 to 4, in combination with a pharmaceutically acceptable carrier.

36. A method according to claim 32 wherein *n* is 1.

37. A method according to claim 32 wherein R is hydrogen.

38. A method according to claim 32 wherein the -CHR-(CH$_2$)$_n$- residue is a -CH$_2$-CH$_2$- group.

39. A method according to claim 32 wherein the compound is 1-(theophyllinyl-7-methylenecarboyloxy)-2-(nicotinoyloxy)ethane.

40. A method according to claim 35 wherein R is hydrogen.

41. A method according to claim 35 wherein *n* is 1.

42. A method according to claim 32 wherein *n* is 1 or 2.

43. A method according to claim 35 wherein *n* is 1 or 2.

44. A method according to claim 32 wherein the compound is 1-(theophyllinyl-7-methylenecarboyloxy)-4-nicotinoyloxy)butane.

45. A method according to claim 32 wherein the compound is 2-(theophyllinyl 7-methylenecarboyloxy)-3-(nicotinoyloxy)propane.

46. A method according to claim 32 wherein administration is oral.

47. A method according to claim 32 wherein the administration is parenteral.

48. A method according to claim 32 wherein the administration is oral and the compound is 1-(theophyllinyl-7-methylenecarboyloxy)-4-(nicotinoyloxy)ethane.

* * * * *